(12) United States Patent  
Dakka et al.

(10) Patent No.: US 7,446,232 B2  
(45) Date of Patent: Nov. 4, 2008

(54) PROCESS FOR OXIDIZING ALKYLAROMATIC COMPOUNDS

(75) Inventors: Jihad Mohammed Dakka, Whitehouse Station, NJ (US); Doron Levin, Highland Park, NJ (US); John Scott Buchanan, Lambertville, NJ (US); Jon Edmond Randolph Stanat, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/827,952

(22) Filed: Jul. 13, 2007

(65) Prior Publication Data

US 2008/0033217 A1  Feb. 7, 2008

Related U.S. Application Data

(60) Provisional application No. 60/835,377, filed on Aug. 3, 2006.

(51) Int. Cl.
*C07C 409/02* (2006.01)
*C07C 37/68* (2006.01)
(52) U.S. Cl. .................. 568/565; 568/570; 568/754
(58) Field of Classification Search ................ 568/565, 568/570, 754
See application file for complete search history.

(56) References Cited

U.S. PATENT DOCUMENTS

| | | | |
|---|---|---|---|
| 3,959,381 | A | 5/1976 | Arkell et al. |
| 4,136,123 | A | 1/1979 | Hutchings |
| 4,255,592 | A | 3/1981 | Kawai et al. |
| 4,282,383 | A | 8/1981 | Dai et al. |
| 4,450,303 | A | 5/1984 | Drake |
| 5,298,667 | A | 3/1994 | Iwanaga et al. |
| 6,720,462 | B2 | 4/2004 | Kuhnle et al. |
| 6,852,893 | B2 | 2/2005 | Kühnle et al. |
| 2003/0083527 | A1 | 5/2003 | Kühnle et al. |
| 2004/0162448 | A1 | 8/2004 | Yang et al. |
| 2004/0236152 | A1 | 11/2004 | Black et al. |

FOREIGN PATENT DOCUMENTS

| | | |
|---|---|---|
| DE | 23 00 903 | 1/1973 |
| EP | 1 088 807 | 4/2001 |
| EP | 1 088 809 | 4/2001 |
| JP | 62/114922 | 11/1985 |
| JP | 2002-282698 | 10/2002 |

OTHER PUBLICATIONS

Haward et al., "Absolute rate constants for hydrocarbon oxidation. VIII. The reactions of cumylperoxy radicals," Canadian Journal of Chemistry, vol. 46, 1968, pp. 1018-1022.

Haward et al., "Absolute rate constants for hydrocarbon oxidation. XI. The reactions of tertiary peroxy radicals," Canadian Journal of Chemistry, vol. 47, 1968, pp. 2655-2660.

Haward et al., "Absolute rate constants for hydrocarbon autoxidation. XIV. Termination rate constants for tertiary peroxy radicals," Canadian Journal of Chemistry, vol. 47, 1969, pp. 3793-3795.

Haward et al., "Absolute rate constants for hydrocarbon autoxidation. XV. The induced decomposition of some t-hydroperoxides," Canadian Journal of Chemistry, vol. 47, 1969, pp. 3797-3801.

Haward et al., "Absolute Rate Constants for Hydrocarbon Autoxidation. XXII. The Autoxidation of some Vinyl Compounds," Canadian Journal of Chemistry, vol. 50, 1972, pp. 2298-2304.

Sheldon et al., "Organocatalytic Oxidations Mediated by Nitroxyl Radicals," Adv. Synth. Catal., 2004, 346, pp. 1051-1071.

Process Economics Program, Stanford Research Institute, entitled "Phenol," Report No. 22B, Dec. 1977, pp. 113-121 and 261-263.

J. K. Kochi, "Chemistry of Alkoxy Radicals: Cleavage Reactions," Journal of the American Chemical Society, vol. 84, 1962, pp. 1193-1197, XP-002460114.

*Primary Examiner*—Sikarl A Witherspoon

(57) ABSTRACT

In a process for oxidizing alkylaromatic compounds to the corresponding hydroperoxide, an alkylaromatic compound of general formula (I):

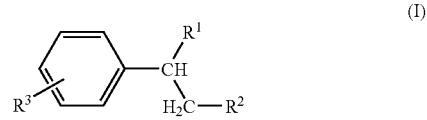

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of an added catalyst comprising tert-butyl hydroperoxide and in the absence of any other catalyst, to produce a hydroperoxide of general formula (II):

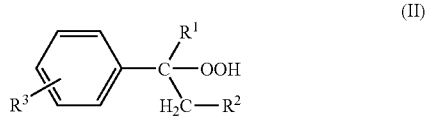

in which $R^1$, $R^2$ and $R^3$ have the same meaning as in formula (I). The hydroperoxide may then be converted into a phenol and a ketone of the general formula $R^1COCH_2R^2$ (III), in which $R^1$ and $R^2$ have the same meaning as in formula (I).

22 Claims, 2 Drawing Sheets

PROCESS FOR OXIDIZING ALKYLAROMATIC COMPOUNDS

CROSS REFERENCE TO RELATED APPLICATION

This application claims priority to U.S. Provisional Patent Application No. 60/835,377, tiled Aug. 3, 2006, the disclosures of which are incorporated herein by reference in its entirety.

FIELD

The present invention relates to a process for oxidizing alkylaromatic compounds and optionally conversion of the product to phenols and ketones.

BACKGROUND

Phenol and substituted phenols are important products in the chemical industry and are useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene relative to that of butenes is likely to increase, due to a developing shortage of propylene.

Thus, a process that uses butenes or higher alkenes instead of propylene as feed and coproduces methyl ethyl ketone (MEK) or higher ketones, such as cyclohexanone, rather than acetone may be an attractive alternative route to the production of phenols. For example, there is a growing market for MEK, which is useful as a lacquer, a solvent and for dewaxing of lubricating oils. In addition, cyclohexanone is used as an industrial solvent, as an activator in oxidation reactions and in the production of adipic acid, cyclohexanone resins, cyclohexanone oxime, caprolactam and nylon 6.

It is known that phenol and MEK can be produced from sec-butylbenzene, in a process where sec-butylbenzene is oxidized to obtain sec-butylbenzene hydroperoxide and the peroxide decomposed to the desired phenol and methyl ethyl ketone. An overview of such a process is described in pages 113-121 and 261-263 of Process Economics Report No. 22B entitled "Phenol", published by the Stanford Research Institute in December 1977.

However, in comparison to cumene, oxidation of aromatic compounds substituted by branched alkyl groups having 4 or more carbon atoms, such as sec-butylbenzene, to the corresponding hydroperoxide requires higher temperatures and is very sensitive to the presence of impurities. For example, in the case of sec-butylbenzene containing 1% by weight of isobutylbenzene, the rate of formation of sec-butylbenzene hydroperoxide decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as low as about 82%.

Thus there remains a need to find an oxidation process for producing $C_4+$ alkyl aromatic hydroperoxides, and particularly sec-butylbenzene hydroperoxide, that is much less sensitive to the presence of impurities than the existing oxidation processes, and that allows efficient commercial scale production of phenol and MEK or higher ketones.

U.S. Pat. No. 5,298,667 (Sumitomo) and EP-A-548,986 (Sumitomo) disclose a process for producing phenol and MEK which comprises the steps of (I) oxidizing a material selected from (A) sec-butylbenzene substantially free from ethyl hydroperoxide, carboxylic acids and phenol, (B) sec-butylbenzene substantially free from styrenes, and (C) sec-butylbenzene substantially free from methylbenzyl alcohol, to obtain sec-butylbenzene hydroperoxide, with an oxygen-containing gas and in the absence of a catalyst, and (II) decomposing the sec-butylbenzene hydroperoxide to obtain phenol and MEK with an acidic catalyst.

EP-A-1,088,809 (Phenolchemie) discloses a process for producing phenol, MEK and acetone by the oxidation of a mixture containing cumene and up to 25 wt % sec-butylbenzene and the subsequent Hock cleavage of the hydroperoxides, so that the ratio of the phenol:acetone:MEK in the product can be controlled via the composition of the feed mixture. The feed mixture is produced directly by the alkylation of benzene with a corresponding mixture of propene and 1-butene/2-butene in the presence of a commercial alkylation catalyst such as $AlCl_3$, $H_3PO_4/SiO_2$ or a zeolite. Oxidation takes place in the presence of air or oxygen and in the absence of a catalyst.

FR-A-2,182,802 (Union Carbide) discloses a process for producing phenol and MEK by oxidation of sec-butylbenzene, in which sec-butylbenzene is oxidized to sec-butylbenzene hydroperoxide in the presence of air and optionally in the presence of sec-butylbenzene hydroperoxide, followed by peroxide decomposition. According to this document, the sec-butylbenzene must not contain more than 1 wt % isobutylbenzene, since the presence of isobutylbenzene significantly reduces the overall process efficiency and hence the yield of phenol and MEK.

Japanese Patent Application Publication No. 62/114922, published May 26, 1987, discloses that sec-butylbenzene can be oxidized with a gas containing molecular oxygen, preferably air, in the presence of cumene or cumene hydroperoxide at a temperature of 90 to 145° C. and a pressure of 1 to 20 $kg/cm^2 G$.

U.S. Patent Application Publications Nos. 2004/0162448 (Shell) and 2004/0236152 (Shell) disclose processes for producing phenol and acetone and/or MEK, in which a mixture of cumene and sec-butylbenzene is oxidized to the corresponding peroxides in the presence of oxygen, followed by peroxide decomposition. In the Examples, the oxidation mixture also contains 1% cumene hydroperoxide as an initiator. According to these documents, the addition of a neutralizing base in the oxidation mixture improves the yield in hydroperoxide and reduces the formation of undesired side products.

U.S. Pat. No. 6,852,893 (Creavis) and U.S. Pat. No. 6,720,462 (Creavis) describe methods for producing phenol by catalytic oxidation of alkyl aromatic hydrocarbons to the corresponding hydroperoxide, and subsequent cleavage of the hydroperoxide to give phenol and a ketone. Catalytic oxidation takes place with oxygen, in the presence of a free radical initiator and a catalyst, typically an N-hydroxycarbodiimide catalyst, such as N-hydroxyphthalimide. Preferred substrates that may be oxidized by this process include cumene, cyclohexylbenzene, cyclododecylbenzene and sec-butylbenzene.

U.S. Pat. No. 4,136,123 (Goodyear) discloses a process for oxidizing alkylaromatic compounds to the corresponding hydroperoxides in the presence of a sulfonated metallo phthalocyanine catalyst and a free radical initiator selected from the group consisting of alkyl hydroperoxides having from 4 to 6 carbon atoms and aralkyl hydroperoxides having from 8 to 14 carbon atoms.

U.S. Pat. No. 4,282,383 (Upjohn) describes a process for making cyclohexylbenzene hydroperoxide useful as an intermediate in the formation of phenol and cyclohexanone. The process involves heating cyclohexylbenzene at a temperature in the range of about 80° C. to about 105° C. in the presence of oxygen and from about 2 to 6 percent by weight, based on cyclohexylbenzene, of a hydroperoxide selected from the group consisting of tertiary-butyl hydroperoxide, cumene hydroperoxide and p-diisopropylbenzene dihydroperoxide, and from about 0.1 to 5 percent by weight, based on cyclohexylbenzene, of a free radical initiator selected from the group consisting of azabisisobutyronitrile, t-butylperbenzoate and dicumyl peroxide.

U.S. Pat. No. 4,450,303 (Phillips Petroleum) describes a process for making secondary alkyl substituted benzene hydroperoxides by heating a secondary alkyl substituted benzene, such as cyclohexylbenzene, cumene, sec-butylbenzene, sec-pentylbenzene, p-methyl-sec-butylbenzene, 1,4-diphenylcyclohexane, para-dicyclohexylbenzene, and sec-hexylbenzene, at a temperature of about 60° C. to 200° C. in the presence of oxygen. The heating is also conducted in the presence of from about 0.05 to 5 wt % of a samarium catalyst of the formula R"COOSm wherein R" is a C1 to C20 alkyl, aryl, alkaryl, or aralkyl radical and optionally a free radical initiator selected from the group consisting of azo-type compounds and peroxide compounds. In one embodiment, the secondary alkyl substituted benzene is cyclohexylbenzene, the catalyst is samarium acetate and the free radical initiator is cumene hydroperoxide.

The article by Sheldlon et al entitled "Organocatalytic Oxidations Mediated by Nitroxyl Radicals" in *Adv. Synth. Catal.*, 2004, 346, pages 1051-1071 discloses that cyclohexylbenzene (CHB) can be oxidized to the 1-hydroperoxide with 97.6% selectivity at 32% CHB conversion at 100° C. in the presence of 0.5 mol % of a N-hydroxyphthalimide catalyst and 2 mol % of the product hydroperoxide as a free radical initiator.

U.S. Pat. No. 3,959,381 (Texaco) discloses a method of preparing phenol and cyclohexanone by contacting a mixture of cyclohexylbenzene and cumene or cumene hydroperoxide at a mole ratio of 1:99 and 99:1 with an oxygen containing gas at a temperature between about 90 and 140° C. and a mole ratio of oxygen to cyclohexylbenzene of at least 3:1 to form a second mixture of 1-phenylcyclohexyl hydroperoxide and cumyl hydroperoxide, and subsequently removing excess cumene and at least a portion of excess cyclohexylbenzene from the second mixture followed by contacting the second mixture with an alkanone of from 3 to 6 carbons and an acid cleavage catalyst selected from hydrocarbyl sulfonic acid and mineral acid at a temperature between about 20 and 50° C. and recovering phenol and cyclohexanone from the final product.

According to the invention, it has now been found that certain secondary alkyl substituted benzenes, including sec-butylbenzene and cyclohexylbenzene, can be oxidized to the corresponding hydroperoxide in the presence of tert-butyl hydroperoxide, but in the absence of other catalysts.

SUMMARY

In one aspect, the present invention resides in a process for oxidizing an alkylaromatic compound to the corresponding hydroperoxide, the process comprising contacting an alkylaromatic compound of general formula (I):

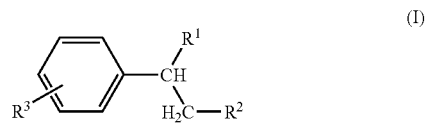

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of an added tert-butyl hydroperoxide catalyst, and in the absence of any other catalyst, to produce a hydroperoxide of general formula (II):

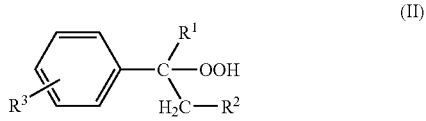

in which $R^1$, $R^2$ and $R^3$ have the same meaning as in formula (I).

In a further aspect, the present invention resides in a process for producing a phenol, said process comprising:

(a) contacting an alkylaromatic compound of general formula (I):

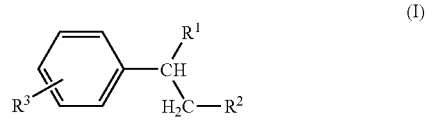

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of an added tert-butyl hydroperoxide catalyst, and in the absence of any other catalyst, to produce a hydroperoxide of general formula (II):

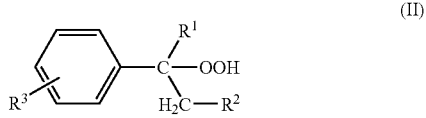

in which $R^1$, $R^2$ and $R^3$ have the same meaning as in formula (I), and (b) converting the hydroperoxide of formula (II) into phenol and a ketone of the general formula $R^1COCH_2R^2$ (III), in which $R^1$ and $R^2$ have the same meaning as in formula (I).

Preferably, said alkylaromatic compound is selected from sec-butylbenzene, sec-pentylbenzene, p-methyl-sec-butylbenzene, 1,4-diphenylcyclohexane, sec-hexylbenzene, and cyclohexylbenzene, and most preferably is sec-butylbenzene or cyclohexylbenzene.

Preferably, said contacting with oxygen is conducted at a temperature of about 20° C. to about 150° C. The oxidation may be with oxygen per se or with a gas comprising molecular oxygen, conveniently air.

DETAILED DESCRIPTION OF THE EMBODIMENTS

Figure 1:
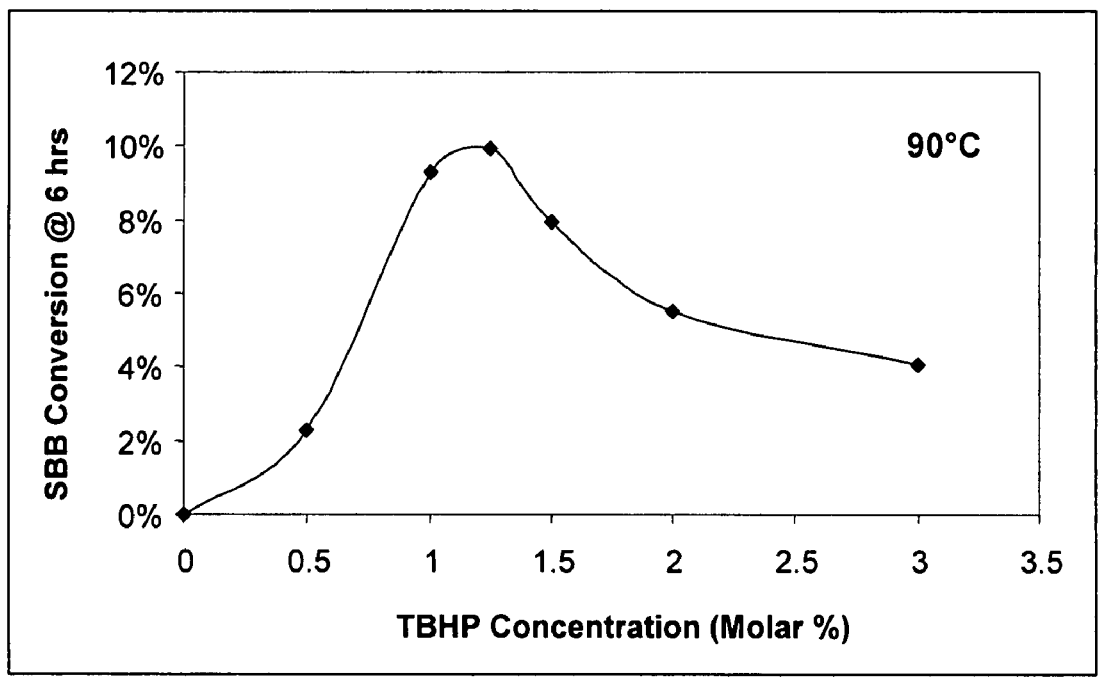
FIG. 1 is a graph of sec-butylbenzene conversion against concentration of added tert-butyl hydroperoxide (TBHP) catalyst in the oxidation process of Example 1.

The present invention provides a process for oxidizing an alkylaromatic compound of general formula (I):

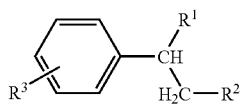

(I)

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group. In an embodiment, $R^1$ and $R^2$ are joined to form a cyclic group having from 4 to 10 carbon atoms, conveniently a cyclohexyl group, substituted with one or more alkyl groups having from 1 to 4 carbon atoms or with one or more phenyl groups. Examples of suitable alkylaromatic compounds are sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

The oxidation is effected by contacting the alkylaromatic compound with oxygen in the presence of an added catalyst comprising tert-butyl hydroperoxide and in the absence of any other catalyst. By "added catalyst" is meant a catalyst that is deliberately added to the oxidation reaction rather than being generated in-situ as part of the reaction. Typically, the tert-butyl hydroperoxide is present in an amount between about 0.05 and about 5 mole %, such as between about 0.5 and about 3 mole %, preferably between about 0.7 and about 2 mole %, more preferably between about 0.8 and about 1.5 mole %, of the combination of the alkylaromatic compound and the tert-butyl hydroperoxide.

The present invention is based on the observation that, in comparison to cumene, oxidation of aromatic compounds substituted by branched alkyl groups having 4 or more carbon atoms, such as sec-butylbenzene, to the corresponding hydroperoxide requires higher temperatures; or in other words, they have a lower oxidation rate. Without wishing to be bound by theory, it is believed that the low oxidation reaction rate of sec-butylbenzene may be attributed to a β scission reaction mechanism. β scission with sec-butylbenzene creates an ethyl radical at a much faster rate than β scission involving cumene (which forms a methyl radical), and terminates the radical reaction at a much faster rate. The rate constants for hydrogen atom abstraction from aralkanes by initiators do not seem to be significantly affected by the aralkane structure (e.g., sec-butylbenzene vs. cumene vs. cyclohexylbenzene). However the aralkane peroxy radicals play vital roles in the termination step. The self-reaction of tertiary peroxy radicals is shown in the following scheme:

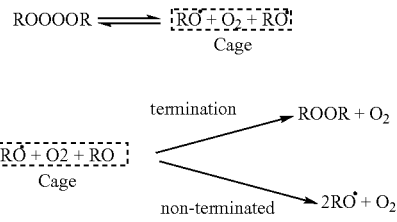

Three factors affecting the termination kinetic process are:
i) The equilibrium constant for R—O—O—O—O—R formation,
ii) Variation in irreversible decomposition of tetroxide, and
iii) Variation in the fraction of alkoxy radical pairs which undergo combination in the solvent cage.

The alkoxy radical (RO.) can undergo β scission, resulting in a ketone and an alkyl radical which reacts with oxygen to give a primary peroxy radical. For example, the alkoxy radical from sec-butylbenzene will yield the ethylperoxy radical and acetophenone. Primary peroxy radicals are generally about 3-5 times more reactive than tertiary peroxy radicals, e.g., in the oxidation of sec-butylbenzene the 2-phenylbutyl-2-peroxy radical will react faster with an ethylperoxy radical than another 2-phenylbutyl radical or abstract a benzylic hydrogen. Also, the stability of the incipient ketone and alkyl radical determine the mode of β scission.

The higher activation energy of the overall termination process reflects the greater rate of alkoxy radical β scission at higher temperature and the greater ease of diffusion of the two alkoxy radicals out from the cage in which they are made. The table below shows the kinetic termination ($k_t$) and propagation ($k_p$) constants for sec-butylbenzene and cumene oxidation. The propagation kinetic constants for both substrates are similar. However, the termination kinetic constant for sec-butylbenzene is 10 times higher than that for cumene.

|  | Cumene | SBB |
|---|---|---|
| $2 k_t * 10^{-3}$ (M$^{-1}$s$^{-1}$) | 1.8 | 18 |
| $k_p$ (M$^{-1}$s$^{-1}$) | 0.14 | 0.16 |

A substance that would minimize the β scission termination reaction will decrease the termination rate constant and as a consequence will improve the reaction rate. Addition of a catalytic amount of initiator is one way to overcome this problem, an elegant and possibly economical solution being the use of tert-butyl hydroperoxide (TBHP). Thus, the rate constant for the chain termination by tert-butylperoxy radical is lower than for any other known alkylperoxy radical. The catalyst used herein (TBHP) does not favor the formation of harmful primary radicals like ethyl or n-propyl. On the other hand, a compound like sec-butylbenzene hydroperoxide would not be considered a suitable oxidation catalyst, since it is prone to form ethyl radicals by scission of the ethyl group that is attached to the benzylic carbon.

Suitable conditions for the present oxidation step include a temperature between about 20° C. and about 150° C., such as about 70° C. to about 130° C., and/or a pressure of about 1 to about 30 atmospheres (100 to 3000 kPa), such as about 1 to about 10 atmospheres (100 to 1000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the hydroperoxide produced may be concentrated by distilling off the unreacted alkylaromatic compound.

The product of the oxidation reaction includes a hydroperoxide of general formula (II):

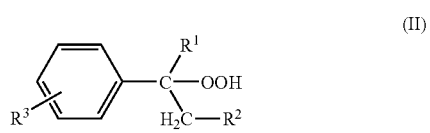

(II)

in which $R^1$, $R^2$ and $R^3$ have the same meaning as in formula (I). Preferably, the hydroperoxide is sec-butylbenzene hydroperoxide or cyclohexylbenzene hydroperoxide. This hydroperoxide can then converted by acid cleavage to phenol or a substituted phenol and a ketone of the general formula $R^1COCH_2R^2$ (III), in which $R^1$ and $R^2$ have the same meaning as in formula (I).

The cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 hr$^{-1}$, preferably about 1 to about 50 hr$^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the following non-limiting Examples.

EXAMPLE 1

SBB Oxidation in the Presence of Tert-Butyl Hydroperoxide (TBHP)

Figure 2:
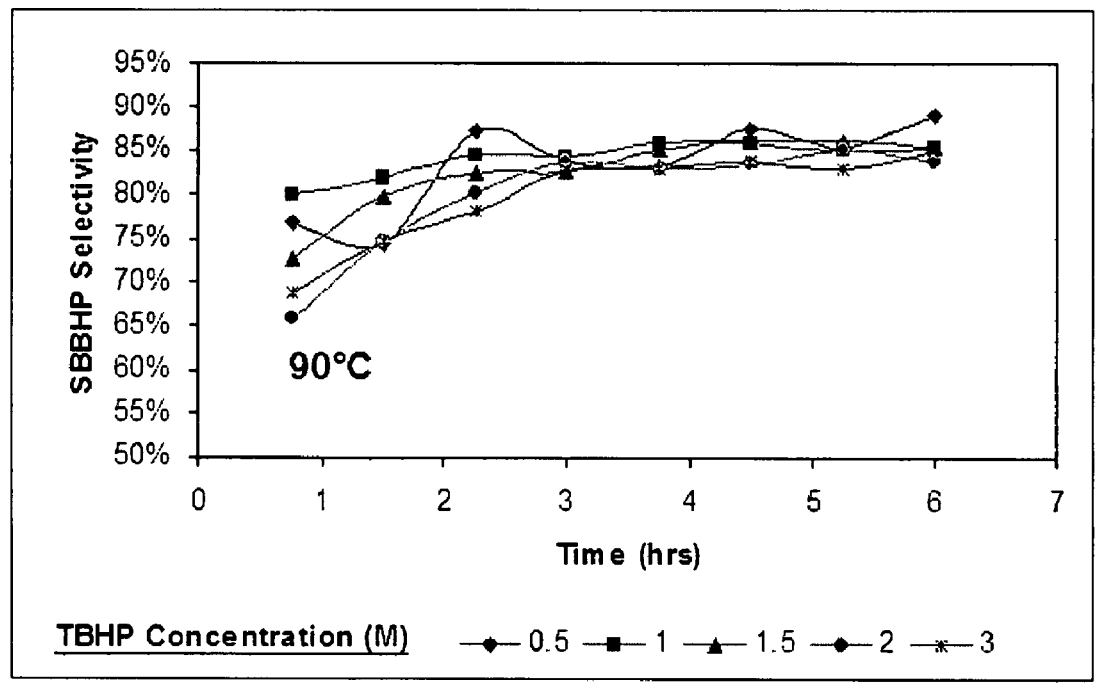
FIG. 2 is a graph of sec-butylbenzene hydroperoxide selectivity against time on stream, with the addition of various amounts of TBHP catalyst in the oxidation process of Example 1.

To a 250-ml round bottom flask fitted with a condenser, stirrer and an air sparger, was charged 100 g of sec-butylbenzene (as supplied by TCI) and a predetermined amount of TBHP. The flask was heated using a temperature-controlled heating mantle. The reaction temperature was 90° C. and the reaction pressure was approximately atmospheric. The air flow rate was approximately 220 cc/min. Every 45 minutes, a small aliquot of the reaction mixture was removed from the flask and analyzed by gas chromatography (GC). The test was run for 6 hrs. The test was repeated with amounts of TBHP varying between 0 and 3 mole % based on the total number of moles of sec-butylbenzene and TBHP and the results are shown in FIGS. 1 and 2. It will be seen from FIG. 1 that the uncatalyzed SBB oxidation showed no conversion and that the highest SBB conversion was obtained at a TBHP concentration was about 1.25 mol %. It will be seen from FIG. 2 that the selectivity to sec-butylbenzene hydroperoxide at the end of the 6 hour test was essentially the same, at 85-90 wt %, at all levels of TBHP tested.

EXAMPLE 2 (Comparative)

SBB Oxidation in the Presence of Cumene Hydroperoxide (CHP)

Figure 3:
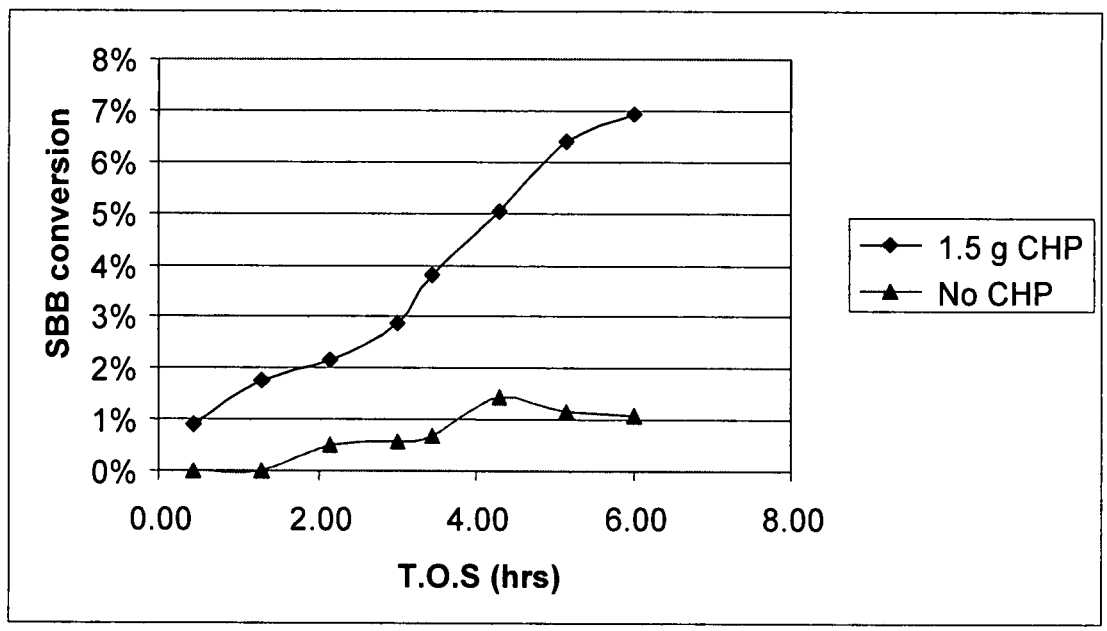
FIG. 3 is a graph of sec-butylbenzene conversion against time on stream, with and without the addition of a cumene hydroperoxide catalyst, in the oxidation process of Example 2.
Figure 4:
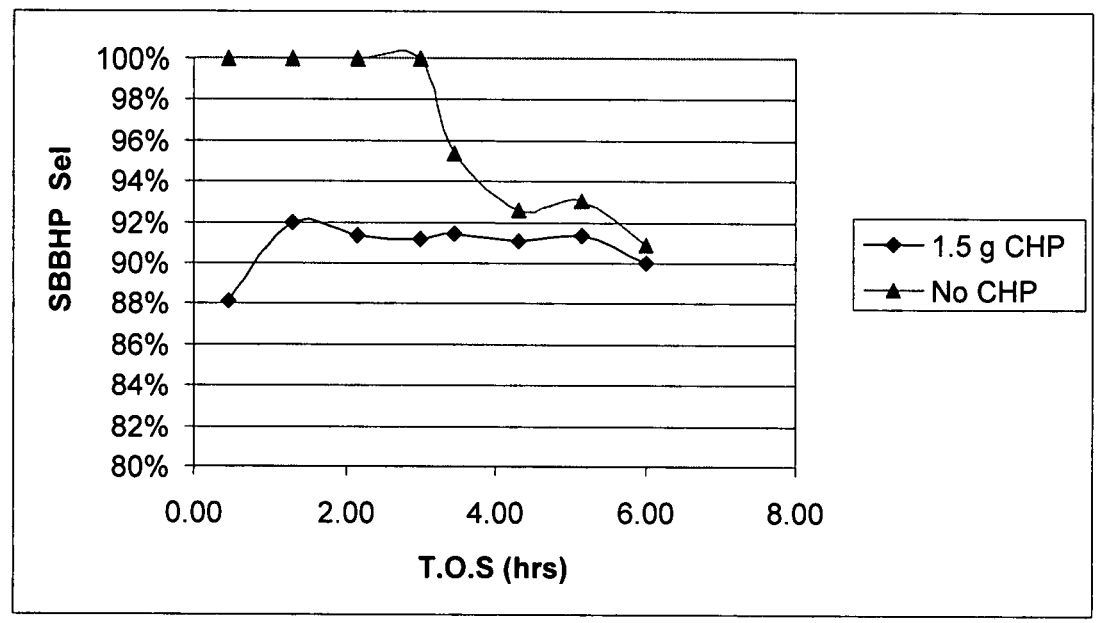
FIG. 4 is a graph of sec-butylbenzene hydroperoxide selectivity against time on stream, with and without the addition of a cumene hydroperoxide catalyst, in the oxidation process of Example 2.

To a 250-ml round bottom flask fitted with a condenser, stirrer and an air sparger, was charged 100 g of sec-butylbenzene (as supplied by TCI) and 1.5 g of cumene hydroperoxide. The flask was heated using a temperature-controlled heating mantle. The reaction temperature was 115° C. and the reaction pressure was approximately atmospheric. The air flow rate was approximately 220 cc/min. Every 45 minutes, a small aliquot of the reaction mixture was removed from the flask and analyzed by GC. The test was run for 6 hrs ("time on stream" or T.O.S.). The test was repeated without the CHP addition and the results of both tests are shown in FIGS. 3 and 4. It will be seen from FIG. 3 that the sec-butylbenzene conversion in the presence of the added CHP was about 7% at the end of the 6 hours of the test, whereas the sec-butylbenzene conversion in the absence of the added CHP was only about 1%. It will be seen from FIG. 4 that the selectivity to sec-butylbenzene hydroperoxide at the end of the 6 hour test was about 90 wt %.

Comparing the results of Examples 1 and 2, although the CHP appeared to be marginally more selective to the hydroperoxide than the TBHP, the significantly higher conversation rate obtained for the TBHP meant an improved overall yield of sec-butylbenzene hydroperoxide by the addition of TBHP as compared with that obtained by the addition of CHP.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for oxidizing an alkylaromatic compound to the corresponding hydroperoxide, the process comprising contacting an alkylaromatic compound of general formula (I):

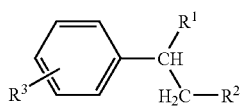

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of an added catalyst comprising tert-butyl hydroperoxide and in the absence of any other catalyst, to produce a hydroperoxide of general formula (II):

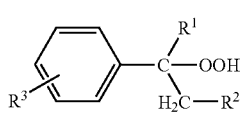

in which $R^1$, $R^2$ and $R^3$ have the same meaning as in formula (I) wherein the tert-butyl hydroperoxide is present in an amount between about 0.5 and about 3 mole % of the combination of the alkylaromatic compound and the tert-butyl hydroperoxide.

2. The process of claim 1, wherein the tert-butyl hydroperoxide is present in an amount between about 0.7 and about 2 mole % of the combination of the alkylaromatic compound and the tert-butyl hydroperoxide.

3. The process of claim 1, wherein said alkylaromatic compound is selected from sec-butylbenzene, sec-pentylbenzene, p-methyl-sec-butylbenzene, 1,4-diphenylcyclohexane, sec-hexylbenzene, and cyclohexylbenzene.

4. The process of claim 1, wherein said alkylaromatic compound is sec-butylbenzene or cyclohexylbenzene.

5. The process of claim 1, wherein said contacting is conducted at a temperature of about 20° C. to about 150° C.

6. The process of claim 1, wherein said contacting is conducted at a temperature of about 70° C. to about 130° C.

7. The process of claim 1, wherein said contacting is conducted at a pressure of about 15 kPa to about 500 kPa.

8. The process of claim 1, wherein said contacting is conducted at a pressure of about 15 kPa to about 150 kPa.

9. A process for producing a phenol, said process comprising:

(a) contacting an alkylaromatic compound of general formula (I):

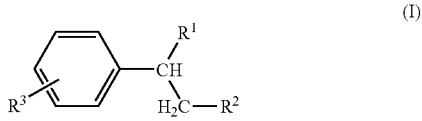

in which $R^1$ and $R^2$ each independently represents an alkyl group having from 1 to 4 carbon atoms, provided that $R^1$ and $R^2$ may be joined to form a cyclic group having from 4 to 10 carbon atoms, said cyclic group being optionally substituted, and $R^3$ represents hydrogen, one or more alkyl groups having from 1 to 4 carbon atoms or a cyclohexyl group, with oxygen in the presence of an added catalyst comprising tert-butyl hydroperoxide and in the absence of any other catalyst, to produce a hydroperoxide of general formula (II):

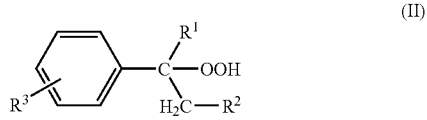

in which $R^1$, $R^2$ and $R^3$ have the same meaning as in formula (I) wherein the tert-butyl hydroperoxide is present in an amount between about 0.5 and about 3 mole % of the combination of the alkylaromatic compound and the tert-butyl hydroperoxide, and (b) converting the hydroperoxide of formula (II) into a phenol and a ketone of the general formula $R^1COCH_2R^2$ (III), in which $R^1$ and $R^2$ have the same meaning as in formula (I).

10. The process of claim 9, wherein the tert-butyl hydroperoxide is present in an amount between about 0.7 and about 2 mole % of the combination of the alkylaromatic compound and the tert-butyl hydroperoxide.

11. The process of claim 9, wherein said alkylaromatic compound is selected from sec-butylbenzene, sec-pentylbenzene, p-methyl-sec-butylbenzene, 1,4-diphenylcyclohexane, sec-hexylbenzene, and cyclohexylbenzene.

12. The process of claim 9, wherein said alkylaromatic compound is sec-butylbenzene or cyclohexylbenzene.

13. The process of claim 9, wherein said contacting is conducted at a temperature of about 20° C. to about 150° C.

14. The process of claim 9, wherein said contacting is conducted at a temperature of about 20° C. to about 130° C.

15. The process of claim 9, wherein said contacting is conducted at a pressure of about 15 kPa to about 500 kPa.

16. The process of claim 9, wherein said contacting is conducted at a pressure of about 15 kPa to about 150 kPa.

17. The process of claim 9, wherein the converting (b) is conducted in the presence of a catalyst.

18. The process of claim 9, wherein the converting (b) is conducted in the presence of a homogeneous catalyst.

19. The process of claim 18, wherein said homogeneous catalyst comprises at least one of sulfuric acid, perchloric acid, phosphoric acid, hydrochloric acid, p-toluenesulfonic acid, ferric chloride, boron trifluoride, sulfur dioxide and sulfur trioxide.

20. The process of claim 9, wherein the converting (b) is conducted in the presence of a heterogeneous catalyst.

21. The process of claim 20, wherein said heterogeneous catalyst comprises a smectite clay.

22. The process of claim 9, wherein the converting (b) is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

* * * * *